United States Patent
Ferone

[19]

[11] Patent Number: 5,945,068
[45] Date of Patent: Aug. 31, 1999

[54] OZONE HAND STERILIZER

[76] Inventor: Daniel A. Ferone, 6038 Oakwood Ave., Cincinnati, Ohio 45224

[21] Appl. No.: 08/619,042

[22] Filed: Mar. 20, 1996

Related U.S. Application Data

[60] Provisional application No. 60/010,625, Jan. 26, 1996.

[51] Int. Cl.[6] .............................. A61L 2/18; E03C 1/05; A47K 1/12
[52] U.S. Cl. .................... 422/28; 422/292; 261/DIG. 42; 4/535; 4/623; 4/626; 134/56 R; 134/95.2; 134/102.3; 34/90; 210/760
[58] Field of Search ................................ 422/28, 29, 292, 422/300, 186.07, 186.12; 4/535, 222, 623, 625, 626, 628; 134/56 R, 201, 11, 31, 37, 90, 95.2, 95.3, 102.1, 102.3; 34/90; 210/760; 261/DIG. 42

[56] References Cited

U.S. PATENT DOCUMENTS

| | | |
|---|---|---|
| 4,606,085 | 8/1986 | Davies . |
| 4,941,270 | 7/1990 | Hoffman ................................ 422/29 X |
| 5,493,743 | 2/1996 | Schneider et al. . |
| 5,514,346 | 5/1996 | Fujita ..................................... 422/124 |
| 5,522,411 | 6/1996 | Johnson .................................. 134/95.2 |
| 5,536,400 | 7/1996 | Schultz ............................ 422/186.12 X |

FOREIGN PATENT DOCUMENTS

| | | |
|---|---|---|
| 2-7967 | 1/1990 | Japan . |
| 6-233805 | 8/1994 | Japan . |
| 2-252461 | 2/1995 | Japan . |

*Primary Examiner*—Elizabeth McKane
*Attorney, Agent, or Firm*—Wood, Herron & Evans, LLP

[57] ABSTRACT

An apparatus and method for sterilizing hands includes a sink containing ozonated water. Water is continually circulated through said sink past an ozone generator which continually injects ozone into the sink. The individual sanitizes his hands by simply immersing his hands in the ozonated water for a period of time effective to destroy germs. Upstream of the sink is a secondary water circulation system which includes a second ozone generator which maintains a constant supply of ozonated water which can be added to the sink when necessary. An infrared sensor can be added to detect when individuals are using the sink and further to determine when make-up water is required. The present invention optionally will include an ozonated air hand drier or an ozonated air applicator for towels. This system is designed to ensure that individuals in, for example, food service operations maintain sanitary conditions.

11 Claims, 1 Drawing Sheet

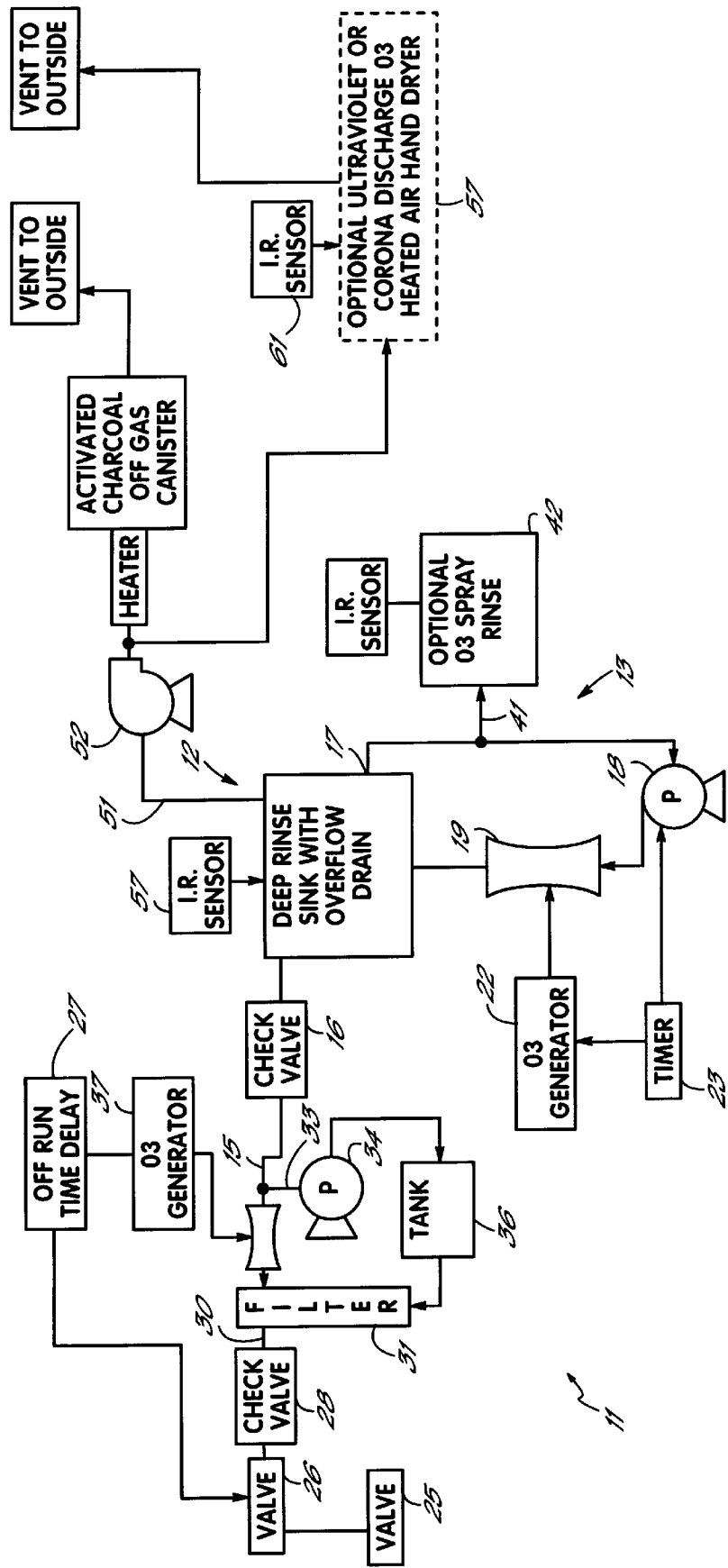

OZONE HAND STERILIZER

This Appln. claims the benefit of U.S. Provisional Appln. No. 60/010,625 filed Jan. 26, 1996.

BACKGROUND OF THE INVENTION

Individuals who work in certain occupations need to have relatively sterile hands. In, for example, food service operations, doctors' offices or dentists' offices, employees must ensure that certain microorganisms are not present on their hands. Activities such as going to the bathroom or handling certain products such as raw meat, particularly chicken, can contaminate the hands with these microorganisms.

The first step to overcome this problem is of course washing the hands. But this is frequently inadequate. In order to kill certain microorganisms, the hand washing solution must be relatively severe, or the hand washing must be extremely thorough. Even so, such a washing operation may not be effective to kill all microorganisms.

Using more severe disinfectants such as alcohol solutions and the like may be more effective, but they are simply too harsh on the skin. Further, they may be relatively dangerous.

SUMMARY OF THE INVENTION

Accordingly, it is an object of the present invention to provide a method to easily clean and sterilize hands. According to the present invention, hands are sterilized by soaking them in a solution of ozonated water. More particularly, the present invention provides an apparatus and method to maintain a water bath with a sufficient concentration of ozone to sterilize hands and is particularly suited for situations wherein multiple users may make use of the apparatus within an abbreviated period of time.

The objects and advantages of the present invention will be further appreciated in light of the following detailed description and drawing in which:

BRIEF DESCRIPTION OF THE DRAWINGS

The FIGURE is a diagrammatic depiction of the apparatus used for the present invention.

DETAILED DESCRIPTION

As shown in the Figure, the present invention is hand sanitizing system 11 which primarily relies on a sink 12 which would be filled with ozonated water. The sink is actually part of a first or primary water circulation system 13. Water is supplied to the primary water circulation system 13 from a secondary water circulation system 14 upstream of the primary water circulation system 13.

The primary water circulation system 13 includes a water inlet 15, which is directed to a check valve 16, which leads to sink 12. Sink 12 has an overflow drain or line 17, which directs overflow water from sink 12 to circulation pump 18. The discharge from the circulation pump 18 leads through a line to a venturi injector 19. The venturi injector, in turn, leads to an inlet 21 into sink 12. About 10–25% of the water flowing through line 17 is discharged through line 41.

The primary water circulation system 13 also includes a first ozonator 22, which injects ozone into the primary circulation system 13 through the venturi injector 19. Both the circulation pump 18 and the ozonator 22 can be operated by various controls. A timer 23 is shown as an exemplary control and its operation is disclosed later herein.

The secondary or upstream water circulation system 14 includes a water inlet 25 which is preferably a tempered water valve which leads to a flow switch 26. The flow switch 26 is controlled by, as shown, a timer 27, whose operation is also discussed below. Downstream of the flow switch 26 is a check valve 28 which leads through line 30 to a filter 31. Check valve 28 allows water to flow only in one direction—from the water inlet 25 to the filter 31. Filter 31 removes particulates from the incoming water. This can be any type of filter which does not cause the degradation of ozone.

Upstream of the filter 31 is a venturi injector 32 which is in line 15. This then leads through line 33 to a pump 34, which discharges through line 35 to a tank 36, which returns back to the filter. The secondary water circulation system 14 also includes an ozone generator 37 which is also operated in response to the timer 27.

Upstream of the primary water circulation system 13 is an overflow line 41 which leads from drain line 17 to discharge excess water from the primary water circulation system. This can either be discharged to a sanitary sewer or may be incorporated into an optional spray rinse 42, as shown in the figure.

Also of concern is the ozone that would be released to the ambient air from above the sink 12. In order to overcome this problem, a vent 51 is directed to a blower 52 which would lead to a heater 53. Ozone is very unstable at elevated temperatures and accordingly would break down in heater 53. This could then be led to a charcoal filter 54 and vented to ambient without causing an unsafe concentration of ozone to exist in any one area.

To use this system, an individual would come to the sink 12 and soak his hands in the sink. An infrared sensor 57 can be employed to detect when an individual uses the sink and could activate a timer (not shown) which would either set off an alarm if an individual did not have his hands in the water for a sufficient period of time, i.e., about 25–30 seconds, or could make a sound indicating this individual can remove his hands from the water. The circulation pump 18 will work continuously to keep the water continuously supplied with ozone. Likewise, ozone generator 22 will be operating constantly at a low setting. Further, check valve 16 will also continuously add a small amount of ozonized water to sink 12.

If the IR sensor 57 detects frequent users, the pump 18 is switched to a higher speed and, likewise, ozone generator 22 can be activated to increase the ozone generation to maintain sufficient supply of ozone to destroy microorganisms.

Further, additional input water can be added by opening check valve 16 from the upstream water circulation system 14. Pump 34 likewise will be constantly circulating at a slow rate to maintain a supply of ozonated water in the secondary water system 14. The tank 36 is optional, but the void space within the tank, along with the void space in the filter 31, maintains a constant supply of water which can be added to the sink 12 through check valve 16 as needed. Again, this can be controlled by the infrared sensor 57 which would detect the number of people using the rinse sink. Accordingly, as determined by a timer and/or as determined by the rate of use detected by IR sensor 57, check valve 16 can be opened, allowing a supply of ozonated water directly into the sink. This could then activate the water inlet flow switch 26. Fresh water being added to the primary circulation system 13 will cause ozone generator 37, which constantly operates at a low rate, to increase its rate of ozone generation to add additional ozone into the system in the secondary water system 14. Once sufficient water is transferred from the secondary system to the primary system, as determined by the timer or the IR sensor, check valve 16 would be closed and the upstream water system would go back into a stand-by mode where the pump 34 operates at a slow speed. This allows for a quick recovery time should a number of people use the sink 14 in a short period of time.

An optional hand air drier 59 would direct air vented through vent line 51 and blower 52 to a hand drier which could include an ultraviolet light to further sanitize hands. This, again, would vent to the outside through vent 61.

In operation of the present invention, the particular flow rates of pumps 18 and 34, either in high or low speed, would be a matter of design optimization. Generally, the concentration of ozone in the water should be maintained at about 4–6 ppm.

The present invention can be further automated. For example, the individuals who are working could be given magnetically coded bracelets or other sensors which would be detected when they entered the bathroom and would also be recognized by the sensor 57, which would ensure that individuals sanitize their hands, as required by company policy. This could be used with the timer to make sure that each individual had his hands in the sink for a sufficient period of time. This would ensure that, as designed by the system, each individual sanitized his hands as necessary to ensure sanitary conditions in the doctor's office, dental office, or food service operation. Overall, this should vastly improve the overall reliability of sanitary conditions in these operations. Further, it requires no chemicals or detergents and is not harsh on the users' hands.

This has been a description of the present invention, along with the preferred method of practicing the invention known to the inventor. However, the invention itself should only be defined by the appended claims wherein we claim:

1. An apparatus for sterilizing hands, comprising:

a sink;

a primary water circulation system fluidly connected to said sink and adapted to fill and continuously recirculate water to and from said sink in contact with hands placed therein;

a first ozone generator fluidly connected to said primary water circulation system for adding ozone to said recirculating water in said sink for sterilizing hands placed therein;

a secondary water circulation system fluidly connected to said primary water circulation system wherein said secondary water circulation system feeds water to said primary circulation system; and a second ozone generator fluidly connected to said secondary water circulation system for adding ozone to the water fed to said primary circulation system.

2. The apparatus claimed in claim 1 wherein at least one of said first and second ozone generators comprises a venturi injector fluidly connected to said respective primary and secondary water circulation systems for injecting ozone into water circulating in said respective primary and secondary water circulation systems.

3. The apparatus claimed in claim 1 further comprising a vent located adjacent said sink and adapted to vent gas above said sink to thereby remove ozone in air above said sink.

4. The apparatus claimed in claim 3 wherein said vent directs said gas to a hand drier.

5. The apparatus claimed in claim 3 wherein said vent directs said gas to a heater.

6. The apparatus claimed in claim 1 further comprising a first sensor adapted to detect when water is needed by said primary water circulation system.

7. The apparatus claimed in claim 6 further including a second sensor adapted to detect when an individual is washing his hands in said sink.

8. The apparatus claimed in claim 7 further comprising an alarm connected to said second sensor, said second sensor including a timer, and wherein said second sensor activates said alarm if said individual does not wash his hands for a predetermined period of time in said sink.

9. A method of sterilizing hands, comprising the steps of:

providing a sink;

filling said sink with ozonated water;

continuously circulating ozonated water to and from said sink from a primary water circulation system;

placing said hands in said filled sink for a period of time to contact said circulating ozonated water and sterilize said hands with said ozonated water;

circulating ozonated water in a secondary water circulation system; and feeding said ozonated water from said secondary water circulation system to said primary water circulation system.

10. The method claimed in claim 9 further comprising drying said hands with ozonated air.

11. The method claimed in claim 9 further comprising applying ozone to towels and drying said hands with said towels.

* * * * *